United States Patent [19]

Burke et al.

[11] Patent Number: 5,670,700
[45] Date of Patent: Sep. 23, 1997

[54] HYDROFORMYLATION PROCESS

[75] Inventors: Patrick Michael Burke, Wilmington, Del.; Onko Jan Gelling, Geleen, Netherlands; Henk Oevering, Stein, Netherlands; Imre Toth, Geleen, Netherlands

[73] Assignees: E. I. Du Pont de Nemours and Company, Wilmington, Del.; DSM, N.V., The Galeen, Netherlands

[21] Appl. No.: 519,835

[22] Filed: Aug. 25, 1995

[51] Int. Cl.⁶ .......................... C07C 67/36; C07C 51/14; C07C 255/00
[52] U.S. Cl. .............. 560/175; 562/522; 558/353
[58] Field of Search .............. 562/522; 560/175; 558/353

[56] References Cited

U.S. PATENT DOCUMENTS

| | | | |
|---|---|---|---|
| 2,549,454 | 4/1951 | Gresham et al. | 560/170 |
| 3,819,669 | 6/1974 | Knifton | 562/522 |
| 4,013,583 | 3/1977 | Knifton | 562/522 |
| 4,733,007 | 3/1988 | Andrale | 502/522 |
| 5,107,015 | 4/1992 | Bertleff et al. | 560/175 |

FOREIGN PATENT DOCUMENTS

| | | |
|---|---|---|
| 4204808 | 2/1992 | Germany. |
| 94/04482 | 3/1994 | WIPO. |

*Primary Examiner*—Paul J. Killos

[57] ABSTRACT

A hydroformylation process for the production of 5-formylvaleric acid from 2-, or 3-pentenoic acid, or 5-formylvaleric acid ester from 2-, or 3-pentenoic acid ester, or 5-formylvaleronitrile from 2-, or 3-pentenenitrile by reaction with hydrogen and carbon monoxide in a solvent containing a catalyst having a platinum component, a bidentate diaryl phosphine component, an acid promoter component.

7 Claims, No Drawings

HYDROFORMYLATION PROCESS

FIELD OF THE INVENTION

This invention relates to the hydroformylation of 2-, or 3-pentenoic acid, 2-, or 3-pentenoic acid esters or 2-, or 3-pentenenitrile to form the corresponding 5-formylvaleric acid, 5-formylvaleric acid ester, or 5-formylvaleronitrile.

BACKGROUND OF THE INVENTION

Botteghi et al. in Journal of Organometallic Chemistry 417 (1991) C41–C45 in an article titled "Hydroformylation of olefins catalyzed by alkene complexes of platinum(O)" disclose hydroformylation using a bidentate phosphino compound, a platinum catalyst, and an acid promoter in an organic solvent. This article notes: ". . . , internal double bonds are rather unreactive as shown by the hydroformylation of cyclohexene . . . "

U.S. Pat. No. 4,528,278 to Hsu describes a hydroformylation catalyst comprising a platinum compound, a ferrocene derived ligand and a Group IV metal halide.

An object of the present invention is to provide a process for the hydroformylation of particular internally unsaturated compounds to form particular linear products.

SUMMARY OF THE INVENTION

The present invention is a process for the preparation of 5-formylvaleric acid, 5-formylvaleric acid ester or 5-formylvaleronitrile which comprises contacting a compound selected from the group consisting of 2-, or 3-pentenoic acid, 2-, or 3-pentenoic acid ester and 2-, or 3-pentenenitrile, with hydrogen and carbon monoxide in an organic solvent for said compound containing a dissolved catalyst comprising (a) a platinum compound free of anionic halide, (b) a bidentate diaryl phosphine ligand having the formula Ar2P—Q—PAr2 where Q is a bivalent bridging group containing 3–5 carbon atoms in which 2 or 3 carbon atoms of the bridge may be part of a cycloalkyl ring containing 3 to 6 carbon atoms or is a ferrocenyl group and each Ar group contains 6 to 15 carbon atoms and (c) an acid promoter selected from (1) sulfonic acids having a pKa in water of less than –2, (2) tetrafluoroboric acid, (3) a fluorine substituted aryl boronic acid of the formula: [HZ]+[B(Ph)4]– where Z is an oxygen containing Lewis base and Ph is a fluorine or trifluoromethyl substituted phenyl group, and (4) hexafluorophosphoric acid and where the ratio (c) to (a) is in the range 0.5/1 to 3/1, and where the ratio of (b) to (a) is in the range 0.6/1 to 1.5/1.

One of the preferred pentenoic acid ester starting materials is methyl-2-pentenoate, or methyl-3-pentenoate and the resulting product is methyl-5-formylvalerate.

Suitable solvents include acetonitrile, adiponitrile, methylglutaronitrile, dimethyladipate, valerolactone, methylisobutylketone, methylene chloride, mixtures of one of the above nitriles and toluene, and homogenous mixtures of the above nitriles and water, sulfones such a sulfolane. Primary and secondary alcohols having up to 6 carbon atoms are also suitable solvents; however, when such an alcohol is the solvent the product will be at least partly the acetal of the 5-formylvaleric acid, 5-formylvaleric acid ester or 5-formylvaleronitrile, but the product will usually also contain some aldehyde. When the process of the present invention is operated in a continuous manner, the product will be removed from the solvent and the solvent recycled, and gradually the composition of the solvent will change as more and more by-products of the reaction remain in the recycled solvent.

The process of the invention is usually carried out temperature is in the range of 80° to 120° C. and the carbon monoxide partial pressure is in the range of 250 to 3000 pounds per square inch.

One of the preferred bidentate diaryl phosphine ligand having the formula Ar2P—Q—PAr2 is 1,1'-bis (diphenylphosphino)ferrocene.

One of the preferred acid promoters is trifluoromethanesulfonic acid.

DETAILED DESCRIPTION

Suitable compounds for hydroformylation into 5-formylvaleric acid ester include pentenoic acid esters such as 2- and 3-pentenoic acid esters where the non-pentenoic acid portion is from a hydrocarbon alcohol. The hydrocarbon alcohol may be saturated or unsaturated, aliphatic or aromatic; but usually will have from 1 to 8 carbon atoms.

Suitable compounds for hydroformylation into 5-formylvaleronitrile include, 2- and 3-pentenenitriles.

Suitable compounds for hydroformylation into 5-formylvaleric acid are 2- and 3-pentenoic acid.

The organic solvent for use in the process should dissolve the platinum catalyst compound, the compound to be hydroformylated, the bidentate diarylphosphine ligand, the acid promoter, and the product. Stated another way, the solvent should provide a homogeneous reaction mixture. Suitable solvents include acetonitrile, adiponitrile, methylglutaronitrile, dimethyladipate, caprolactone, dichloromethane, 2-butanone propylenecarbonate, valerolactone, methylisobutylketone, sulfolane, methylene chloride, mixtures of one of the above nitriles and toluene, and homogenous mixtures of the above nitriles and water. Primary and secondary alcohols having up to 6 carbon atoms are also suitable solvents; however, when such an alcohol is the solvent the product will be at least partly the acetal of the 5-formylvaleric acid, 5-formylvaleric acid ester or 5-formylvaleronitrile, but the product will usually also contain some aldehyde. When the process of the present invention is operated in a continuous manner, the product will be removed from the solvent and the solvent recycled, and gradually the composition of the solvent will change as more an more by-products of the reaction remain in the recycled solvent.

The platinum component of the catalyst must be free of anionic halide, but may contain covalent halide, e.g. fluorinated beta-diketonate. Platinum(II) beta-diketones, platinum (II)carboxylates, and platinum complexes such as Pt(cyclooctadiene)2 may be the platinum catalyst component.

The acid promoter component of the catalyst is selected from (1) sulfonic acids having a pKa in water of less than –2, (2) tetrafluoroboric acid, (3) a fluorine substituted aryl boronic acid and (4) hexafluorophosphoric acid, and hexafluoroantimonic acid. Trifluoromethanesulfonic acid is one of the preferred acids. Some acids of the formula: HB(Ar)4, specifically [(3,5-(CF3)2C6H3)4B]-[H(OET)2)]+ are also quite effective. (This is the etherate solvate of the free acid). See: Brookhart, M.; Grant, B.; and Volpe, Jr., A. F. Organometallics, 1992, 11, 3920.)

The bidentate diaryl phosphine ligand having the formula Ar2P—Q—PAr2 where Q is a bivalent bridging group containing 3–5 carbon atoms in which 2 or 3 carbon atoms of the bridge may be part of a cycloalkyl ring containing 3 to 6 carbon atoms or is a ferrocenyl group and each Ar group contains 6 to 15 carbon atoms include such compounds as 1,4-Bis(diphenylphosphino)butane, (+)2,3-O-Isopropylidine-2,3-dihydroxy-1,4-bis(diphenyl phosphino) butane, (−)-(2S,4S)-2,4-Bis(diphenylphosphino)pentane, 1,3-Bis(diphenylphosphino)propane, (S)-(−)-2,2'-Bis (diphenylphosphino)-1,1'binapthyl; 1,1-Bis (diphenylphosphino)ferrocene; 1,1'-Bis(di-m-fluorophenylphosphino)ferrocene; 1,1'-Bis(di-p-methylphenylphosphino)ferrocene; 1,1'-Bis(diphenylphosphino)3,3'-(trimethylsilyl)ferrocene; 1,1'-Bis(di-p-trifluoromethylphenylphosphino)ferrocene; and, 1,1'-Bis(di-3,5(bis(triflouromethyl)phenylphosphino)ferrocene.

The ferrocenyl ligand and the acid may be combined as in in the neutral complex (DPPF)PtC2H4 where DPPF is 1,1'-bis(diphenylphosphinoferrocene). The anion of the acid, the ligand and the Pt may also be combined into a single complex such as in [(DPPF)Pt(AcAc)][OSO3CF3] where AcAc is the acetylacetonate anion and OSO3CF3 is the anion derived from trifluoromethane sulfonic acid. Such compounds may be formed in-situ for example by combining equimolar amounts of Pt(AcAc)2, trifluoromethane sulfonic acid and DPPF in a solvent such as acetonitrile-toluene mixtures.

In order to be most effective the ratio of acid promoter to platinum compound should be is in the range 0.5/1 to 5/1, and the ratio of bidentate diaryl phosphine ligand to platinum compound should be in the range 0.6/1 to 1.5/1. The platinum component should be in the reaction mixture to the extent of about 500 to 5000 parts per million parts of the reaction mixture. Usually the amount of platinum component will be about 2000 parts per million parts of the reaction mixture.

The process can be operated at a temperature range of 80° to 120° C., and at a pressure of 250 to 3000 pounds per sq inch.

EXAMPLE 1

M3P Hydroformylation with (DPPF)PtC2H4+ DPPF+Trifluoromethane Sulfonic (Triflic Acid) in 4/1 Toluene-acetonitrile Solvent A 25 ml glass lined shaker tube was charged with 5 ml of a solution containing 11.4 g (100 mmole) methyl-3-pentenoate (M3P), 0.777 g (1.0 mmole) 1,1'-Bis (diphenylphosphino)ferrocenyl (ethylene) Platinum ((DPPF)Pt(C2H4)) 0.120 g (0.2 mole) 1,1'-Bis (diphenylphosphino)ferrocene, 0.120 mg (70 μl; 0.8 mmoles) trifluoromethane sulfonic acid also referred to as triflic acid (CF3SO3H), 0.36 g (20 moles) water and 1.00 g o-dichlorobenzene (ODCB, internal GC standard) in 100 ml of a 4:1 mixture of toluene and acetonitrile. The solution contained 0.05 mg-atom Pt and a Pt/DPPF/Triflic/water mole ratio of 1:1.25:0.8:20.

The shaker tube was freed from air by pressurizing and depressurizing first with 100 psi nitrogen (twice) and then with 1:1 CO/H2 (twice). The tube was then pressurized to 700 psi CO/H2 and heated 100° C. over 30 minutes. The pressure was then adjusted with 1:1 CO/H2 to 1000 psi at 100° C. The temperature was maintained at 100° C. with shaker agitation for 2 hours. The heat was shut off and the shaker tube was allowed to cool to 25°–35° C. The excess CO/H2 was vented and the product was analyzed for methyl esters and formylvalerates on a capillary GC column. The analysis showed:

| M3P Conversion | 35.0% |
|---|---|
| Selectivities | |
| Methyl-5-formylvalerate (M5FV) | 87.8 |
| Methyl-4-formylvalerate (M4FV) | 5.6 |
| Methyl-3-formylvalerate (M3FV) | 1.2 |
| Cis- and trans-methyl-2-pentenoate (TM2P) | 2.6 |
| Methylvalerate (MV) | 3.1 |
| Accounting (sum of all analyzed products and starting material): | 98% |

The results demonstrate the very high yield of linear product from an internal olefin using the above platinum catalyst. Thus, the yield to the desired product, methyl-5-formylvalerate (M5FV), is >86% at 35% conversion and the linearity (100*MSFV/(MSFV+M4FV+M3FV)) is 93.1%.

Note: Selectivity to a product is defined here as:

100*(Moles Product)/Sum of (moles of all products detected by the GC analysis).

If the accounting is 100%, then selectivity is the same as yield. If the accounting is less than 100% then the yield= Selectivity*Accounting/100. Thus, in the above example, Yield=87.8*98/100 or 86.04%. Lower than 100% accounting could be due, in part, to analytical error (+or −1–2%) or to formation of non-volatile products, e.g., high molecular weight aldol condensation products or acetals which are not analyzed by the GC method.

In the following examples the products were analyzed in the same way but the results are expressed in summary form as combined conversion of M3P and M4P ("Conv"), Selectivity to methyl-5-formylvalerate ("Sel"), linearity ("lin") and product accounting ("Acctg").

EXAMPLE 2

(Lower Ratio of Ligand to Pt)

M3P Hydroformylation with (DPPF)PtC2H4+Triflic Acid at 100° C.

The experiment in Example 1 was repeated except that the excess DPPF ligand was omitted, i.e., the mole ratio of DPPF to Pt was 1.0. The results are shown in Table 1.

EXAMPLE 3

(A Higher MW Perfluorosulfonic Acid)

M3P Hydroformylation with (DPPF)PtC2H4+ DPPF+Perfluoro-octanesulfonic Acid (PFOSA) at 100° C.

The experiment in Example 1 was repeated except that the triflic acid was replaced with perfluoro-octanesulfonic acid (5 moles per mole Pt complex). The results are shown in Table 1.

EXAMPLES 4–5

(Different Pressures)

M3P Hydroformylation with (DPPF)PtC2H4+Triflic Acid at 100° C. and 800 psi

The experiment in Examples 1 and 2 were repeated except that the pressure was reduced to 800 psi and the ligand to Pt ratio was varied. The results are shown in Table 1.

TABLE 1

| Ex. | Press (psi) | L/Pt | Acid | Acid/Pt | Conv | sel | Lin | Acctg |
|---|---|---|---|---|---|---|---|---|
| 1 | 1000 | 1.2 | TfOH | 0.8 | 35.0 | 87.8 | 91.7 | 98 |
| 2 | 1000 | 1.0 | TfOH | 0.8 | 55.7 | 83.5 | 91.8 | 96 |
| 3 | 1000 | 1.2 | PFOSA | 5.0 | 13.8 | 94.1 | 91.1 | 96 |
| 4 | 500 | 1.25 | TfOH | 0.8 | 59.2 | 86.9 | 93.8 | 99 |
| 5 | 250 | 1.25 | TfOH | 0.8 | 34.2 | 77.7 | 94.2 | 98 |

The above results demonstrate that high yields can be obtained with other strong acids, at different ratios of ligand to Pt and a pressures down to 250 psi 1:1 CO/H2.

EXAMPLES 6–9

(Different Pentenoate Isomer)

Hydroformylation of Methyl-2-Pentenoate (M2P) with (DPPF)PtC2H4+DPPF+Triflic Acid The experiment in Example 1 was repeated except that the M3P was replaced with methyl-2-pentenoate (M2P) and the temperature, pressure and ligand to Pt ratio were varied. The results are shown in Table 2.

TABLE 2

| Ex. | Olefin | L/Pt | Temp | Press | Conv | Sel | Lin | Acctg |
|---|---|---|---|---|---|---|---|---|
| 6 | M2P | 1.0 | 100 | 1000 | 15.9 | 77.7 | 92.8 | 98 |
| 7 | M2P | 1.2 | 100 | 1000 | 15.2 | 75.0 | 92.3 | 99 |
| 8 | M2P | 1.2 | 100 | 600 | 15.4 | 76.5 | 94.3 | 98 |
| 9 | M2P | 1.2 | 110 | 1000 | 17.0 | 75.7 | 93.0 | 97 |

The above results demonstrate that high yields can be obtained with this catalyst system even with a conjugated internal olefin (M2P).

EXAMPLE 10

(High Substrate Concentration, High Boiling Nitrile Solvent, Use of Pt(AcAc)2 Platinum Precursor)

M3P Hydroformylation at Very High Concentration with Pt(AcAc)2+DPPF+Triflic Acid in Adiponitrile at 100° C. and 1000 psi A 100 ml mechanically stirred Hastelloy-C autoclave was flushed with nitrogen and then with 1:1 CO/H2. It was then charged with a nitrogen sparged solution at 0.197 g (0.5 mmoles) Pt(AcAc)2, 0.35 g (0.62 mole) DPPF ligand, 0.068 g (0.45 mmole) triflic acid promoter 0.50 g ODCB internal GC standard and 10.8 g (200 mmole) adiponitrile in 38.1 g (334 mmole) methyl-3-pentenoate (M3P). The autoclave was pressured with 1:1 CO/H2 to 800 psi and heated to 100° C. The pressure was adjusted with 1:1 CO/H2 to 1000 psi at 100° C. CO/H2 was continuously fed to the autoclave from a reservoir so as to maintain the total pressure constant at 1000 psi. Samples were removed at intervals for GC analysis. The reaction was allowed to run for a total of 24 hours after which it was cooled to 20° C. The excess CO/H2 was vented through a control valve and the product was discharged.

The samples from the reactor were analyzed on a 30 m Carbowax capillary GC column. The results are shown in Table 2.

| Time (min) | Conversion (%) | Selectivity (% M5FV) | Linearity (%) |
|---|---|---|---|
| 60 | 6.5 | 59.3 | 93.0 |
| 125 | 22.3 | 82.2 | 92.6 |
| 180 | 34.7 | 87.2 | 92.5 |
| 250 | 48.6 | 87.3 | 92.4 |
| 370 | 66.7 | 85.2 | 92.2 |
| 1485 | 99.9 | 74.5 | 91.8 |

The first order rate constant is 0.21/Hr and the mover frequency based on this rate is 101 moles M3P converted/mole Pt/hour.

The results indicate that reaction can be run successfully at very high substrate concentrations (up to at least 76% M3P) in the presence of a Nitrile co-solvent which has a boiling point higher than the product, M5FV. Thus the product, M5FV, can be separated from the catalyst and the catalyst-nitrile solution can be recycled.

EXAMPLES 11–15

(Different Solvents)

Hydroformylation of Methyl-3-Pentenoate with (DPPF)PtC2H4+DPPF+Triflic Acid in Different Solvents The experiment in Example 1 was repeated except that the solvent was varied, the water was omitted and the concentration of M3P was 5.0M. The results are shown in Table 3.

TABLE 3

| Ex. | Solvent | Conv | Sel | Lin | Acctg |
|---|---|---|---|---|---|
| 11 | Valeronitrile | 31.4 | 88.9 | 93.3 | 96.3 |
| 12 | 2-Butanone | 24.1 | 84.1 | 91.2 | 94.6 |
| 13 | Dichloromethane | 19.7 | 79.4 | 90.3 | 98.3 |
| 14 | Caprolactone | 15.5 | 84.0 | 90.8 | 97.9 |
| 15 | Propylenecarbonate | 13.7 | 79.8 | 90.3 | 98.3 |

The above results demonstrate that high yields can be obtained in both polar and non-polar solvents.

EXAMPLES 16–20

(M3P with Various Bidentate Phosphine Ligands)

The experiment in Example 1 was repeated except that the platinum precursor was platinum(II) acetylacetonate, Pt(AcAc)2, the DPPF ligand was replaced with various bidentate phosphine ligands, the water was omitted, and the reaction was allowed to run for 6 hours. The results are shown in Table 4.

TABLE 4

| Ex. | Ligand | Lig/Pt | Conv | Sel | Lin | Acctg |
|---|---|---|---|---|---|---|
| 16 | DPPB | 1.0 | 49.1 | 72.4 | 86.6 | 96 |
| 17 | DIOP | 1.25 | 81.4 | 66.6 | 82.1 | 90 |
| 18 | (SS)-BDPP | 1.0 | 88.6 | 74.4 | 87.8 | 96 |
| 19 | DPPP | 1.0 | 62.3 | 57.3 | 64.9 | 100 |
| 20 | BINAP | 0.5 | 14.5 | 52.7 | 75.3 | 96 |

*Run at 600 psi
DPPB = 1,3-Bis(diphenylphosphino)butane
DIOP = (+)2,3-O-Ispropylidine-2,3-dihydroxy-1,4-bis(diphenylphosphino)butane

TABLE 4-continued

| Ex. | Ligand | Lig/Pt | Conv | Sel | Lin | Acctg |
|---|---|---|---|---|---|---|

(S,S)-BDPP = (−)-(2S,4S)-2,4-Bis(diphenylphosphino)pentane
DPPP = 1,3-Bis(diphenylphosphino)propane
BINAP = (S)-(−)-2,2'-Bis(diphenylphosphino)1,1'-binaphthyl

EXAMPLES 21–27

(Different Acid Promoters at Low (1M) Substrate Conc))

The experiment in Example 1 was repeated except that the platinum catalyst precursor was platinum(II) acetylacetonate, Pt(AcAc)2, the water was omitted and the triflic acid was replaced with different strong acids in different mole ratios to the platinum precursor. The results are summarized in Table 5.

TABLE 5

| Ex. | Acid | Acid/Pt | Ligand | H₂O/Pt | Conv | Sel | Lin |
|---|---|---|---|---|---|---|---|
| 21 | Triflic | 1.0 | DPPF | 0 | 33.1 | 94.6 | 93.0 |
| 23 | PFOSA | 5 | DIOP | 50 | 33.3 | 71.2 | 79.8 |
| 24 | p-TSA | 3.0 | DPPF | 0 | 35.7 | 82.6 | 91.8 |
| 25 | MSA | 2.0 | DPPF | 0 | 52.2 | 79.1 | 91.9 |
| 26 | HBF4 (54% aq) | 1.0 | DPPF | 50 | 30.5 | 86.7 | 90.8 |
| 27 | HPF6 (60% Aq) | 1.0 | DPPF | 50 | 28.0 | 87.7 | 91.8 |

Triflic = Trifluoromethanesulfonic acid
p-TSA = p-Toluenesulfonic acid (monohydrate)
MSA = Methanesulfonic acid
PFOSA = Perfluorooctanesulfonic acid

EXAMPLE 28

HBARF* at High (6M) M3P Concentration

A 25 ml glass lined shaker tube was charged with a 5 ml aliquot of an acetonitrile solution containing 68.4 g (600 mmole) methyl-3-pentenoate, 0.393 g (1.0 mmole) Platinum acetylacetonate (Pt(AcAc)2) and 1.0 g tetradecane (internal GC standard) in 100 ml. To this solution was added 35 mg (1.25 mmole per Pt) of 1,1'-Bis(diphenylphosphino)ferrocene and 39 mg (0.9 mmoles per Pt)of H(BARF).

The shaker tube was freed from air by pressurizing and depressurizing first with 100 psi nitrogen (twice) and then with 1:1 CO/H2 (twice). The tube was then pressurized to 700 psi (CO/H2 and heated 100° C. over 20 minutes. The pressure was then adjusted with 1:1 CO/H2 to 1000 psi over 100° C. The temperature was maintained at 100° C. with shaker agitation for 6 hours. The heat was shut off and the shaker tube was allowed to cool to 25°–35° C. The excess CO/H2 was vented and the product was analyzed for methyl esters and formylvalerates on a capillary GC column. The results are summarized in Table 6.

*HBARF=[(3,5-(CF₃)₂C₆H₃)₄B]⁻[H(OEt)₂)₂]⁺(Ref. Brookhart, M., et al., Organometallics, 1992, 11, 3920–3922.)

EXAMPLES 29–33

Other Strong Acids at High (6M) M3P Concentration

The experiment in Example 28 was repeated except that the temperature, acid and ligand were varied. The results are shown in Table 6.

TABLE 6

| Ex | Temp | Acid | Acid/Pt | Ligand | Lig/Pt | Conv | Sel | Lin |
|---|---|---|---|---|---|---|---|---|
| 28 | 100 | HBARF | 0.9 | DPPF | 1.25 | 43.5 | 84.0 | 91.9 |
| 29 | 100 | Triflic | 0.8 | DPPF | 1.25 | 67.0 | 84.5 | 92.3 |
| 30 | 100 | HBARF | 1.0 | DIOP | 1.25 | 51.4 | 66.8 | 86.0 |
| 31 | 110 | HBF4 (54% aq) | 1.0 | DPPF | 1.32 | 54.3 | 76.7 | 89.6 |
| 32 | 110 | HSbF (6H2O) | 1.0 | DPPF | 1.32 | 51.8 | 58.5 | 81.3 |
| 33 | 110 | HPF6 (60% aq) | 1.0 | DPPF | 1.32 | 65.8 | 72.0 | 89.0 |

The results indicate that a variety of weakly coordinating acids are effective promoters.

EXAMPLES 34–35

Use of (DPPF)Pt(AcAc)OTf as Pt, Ligand and Acid Sources

The complex (DPPF)Pt(AcAc)OTf was isolated as an orange colored solid by allowing equimolar amounts (0.1 mmoles) each of DPPF ligand, Pt(AcAc)2 and triflic acid to stand in 10 ml of a 4/1 mixture of toluene and acetonitrile over 24 hours. The experiment in Example 28 was then repeated except that the Pt(AcAc)2, DPPF and triflic acid were replaced with an equimolar amount of the isolated (DPPF)Pt(AcAc)OTf complex. In another experiment additional DPPF was also added. The results are shown in Table 7.

TABLE 7

| Ex | Pt Source | Ligand | Lig/Pt | Conv | Sel | Lin |
|---|---|---|---|---|---|---|
| 34 | (DPPF)Pt(AcAc)OTf | None | 0 | 50.5 | 65.8 | 83.3 |
| 35 | (DPFF)Pt(AcAc)OTf | DPPF | 0.25 | 34.5 | 76.0 | 88.3 |

The results show that the isolated complex is active and selective without any additional ligand or acid promoter and that addition of a small amount of DPPF ligand (0.25 equivalents) increases the selectivity.

EXAMPLES 36–41

(3-Pentenoic Acid Hydroformylation

The experiment in Example 1 was repeated except that the methyl-3-pentenoate was replaced with an equivalent amount of 3-pentenoic acid, the platinum source was Pt(AcAc)2 and the water and acid promoter were varied. The products were analyzed directly as the formyl acids on a capillary GC column. The results are summarized in Table 8.

TABLE 8

| Ex | Acid | Acid/Pt | Ligand | Lig/Pt | H₂O/Pt | Conv | Sel to 5FVA | Lin |
|---|---|---|---|---|---|---|---|---|
| 36 | Triflic | 0.8 | DPPF | 1.25 | 50 | 83.3 | 85.1 | 91.0 |
| 37 | Triflic | 1.0 | DPPF | 1.25 | 50 | 71.4 | 65.7 | 83.2 |
| 38 | Triflic | 1.0 | DPPF | 1.25 | 0 | 66.3 | 49.5 | 72.7 |
| 39 | HBF4 (54% aq) | 1.0 | DPPF | 1.25 | 50 | 69.1 | 81.9 | 90.7 |
| 40 | HPF6 (60% aq) | 1.0 | DPPF | 1.25 | 50 | 80.3 | 83.8 | 90.8 |
| 41 | PFOSA | 5.0 | DPPF | 1.25 | 50 | 90.2 | 83.6 | 90.1 |

The results show that very high yield of 5-formylvaleric acid (5FVA) can be obtained from 3-pentenoic acid with the acid promoted platinum catalysts of this invention. Further, it can be seen that yields are improved by adding a small quantity of water (e.g., about 50 equivalents of water per equivalent of Pt).

EXAMPLES 42–45

(3PN Hydroformylation)

The experiment in Example 1 was repeated except that the M3P was replaced with 3-pentenenitrile (3PN), the platinum catalyst precursor was platinum(II) acetylacetonate, Pt(AcAc)2, the mole ratio of water to Pt was 20 and the ligand was varied. The products (formylvaleronitriles and valeronitrile) were analyzed directly by capillary GC. The results are summarized in Table 9.

TABLE 9

| Ex | Ligand | Lig/Pt | Conv | Sel to 5FVN | Lin | Acctg |
|---|---|---|---|---|---|---|
| 42 | DPPF | 1.25 | 9.3 | 76.8 | 92.2 | 99 |
| 43 | DPPB | 1.25 | 2.9 | 35.8 | 64.8 | 99 |
| 44 | DIOP | 1.25 | 8.6 | 64.9 | 78.1 | 99 |
| 45 | SS-BDPP | 1.25 | 7.4 | 47.1 | 61.0 | 98 |

The results show that 3PN gives primarily linear product with this catalyst system.

EXAMPLE 46

(M3P Hydroformylation in Methanol Solvent: Formation of Acetals of 5-Formlvaleric Acid Methyl Ester)

A 25 ml glass lined shaker robe was charged with a 5 ml aliquot of a methanol solution containing 34.2 g (300 mole) methyl-3-pentenoate, 0.393 g (1.0 mmole) Platinum acetylacetonate (Pt(AcAc)2) and 1.0 g tetradecane (internal GC standard) in 100 ml of solution. To this solution was added 37 mg (1.32 mmole per Pt) of 1,1'-Bis(diphenylphosphino) ferrocene and 7.5 mg (1.0 mmoles per Pt) of triflic acid.

The shaker tube was freed from air by pressurizing and depressurizing first with 100 psi nitrogen (twice) and then with 1:1 CO/H2 (twice). The tube was then pressurized to 700 psi CO/H2 and heated 100° C. over 20 minutes. The pressure was then adjusted with 1:1 CO/H2 to 1000 psi at 100° C. The temperature was maintained at 100° C. with shaker agitation for 6 hours. The heat was shut off and the shaker tube was allowed to cool to 25°–35° C. The excess CO/H2 was vented and the solution was analyzed by capillary GC. The product was a mixture of the linear and branched formylvalerates and their methyl acetals. The approximate conversions and selectivity for linear products are given in Table 10.

EXAMPLE 47

(M3P Hydroformylation in Methanol Solvent: Higher Triflic Acid/Pt Ratio)

The experiment in Example 4 was repeated except that the ratio of triflic acid to Pt was increased to 5/1. The results are shown in Table 10.

TABLE 10

| Ex | Acid | Acid/Pt | Ligand | Lig/Pt | Conv | Sel to linear Pdts | Lin |
|---|---|---|---|---|---|---|---|
| 46 | Triflic | 1.0 | DPPF | 1.25 | 63.5 | 84.8 | 88.2 |
| 47 | Triflic | 5.0 | DPPF | 1.25 | 68.7 | 53.5 | 76.3 |

The results show that the linear products predominate in methanol solvent and that the acid promoter for the hydroformylation reaction also promotes the acetalization reaction.

EXAMPLE 48

M3P Hydroformylation in Sulfolane Solvent with DPPF Ligand

The experiment in Example 28 was repeated except that the solvent was sulfolane, the internal standard was omitted, and the acid promoter was triflic acid (0.8 equivalents per g-atom of Pt). A catalytic amount of acetonitrile (103 mg/5 ml solution; 50 equivalents per g-atom of Pt) was also added. Analysis of the reaction mixture using an external tetradecane standard in tetrahydrofuran gave the results shown in Table 11.

EXAMPLES 49–52

M3P Hydroformylation in Sulfolane Solvent with Alternate Ligands

The experiment in Example 48 was repeated except that the ligand and ratio of ligand to Pt were varied. The results are summarized in Table 11.

TABLE 11

| Ex | Ligand | Lig/Pt | Conv | Sel to M5FV | Lin |
|---|---|---|---|---|---|
| 48 | DPPF | 1.25 | 32.0 | 86.9 | 91.3 |
| 49 | DPPB | 1.00 | 17.9 | 73.5 | 87.4 |
| 50 | DIOP | 1.25 | 22.0 | 77.3 | 85.4 |
| 51 | DPPP | 1.00 | 8.2 | 60.1 | 73.6 |
| 52 | SS-BDPP | 1.00 | 15.2 | 72.3 | 85.2 |

The data show that high selectivities to the linear aldehyde M5FV, can be obtained in sulfolane solvent with a variety of bidentate phosphine ligands.

We claim:

1. A process for the preparation of 5-formylvaleric acid, 5-formylvaleric acid ester or 5-formylvaleronitrile which comprises contacting a compound selected from the group consisting of 2-, or 3-pentenoic acid, 2-, or 3-pentenoic acid ester and 2-, or 3-pentenenitrile, with hydrogen and carbon monoxide in an organic solvent for said compound containing a dissolved catalyst comprising (a) a platinum compound free of anionic halide, (b) a bidentate diaryl phosphine ligand having the formula Ar2P—Q—PAr2 where Q is a bivalent bridging group containing 3–5 carbon atoms in which 2 or 3 carbon atoms of the bridge may be part of a cycloalkyl ring containing 3 to 6 carbon atoms or is a ferrocenyl group and each Ar group contains 6 to 15 carbon atoms and (c) an acid promoter selected from (1) sulfonic acids having a pKa in water of less than −2, (2) tetrafluoroboric acid, (3) a fluorine substituted aryl boronic acid of the formula: [HZ]+[B(Ph)4]− where Z is an oxygen containing Lewis base and Ph is a fluorine or trifluoromethyl substituted phenyl group, and (4) hexafluorophosphoric acid and where the ratio (c) to (a) is in the range 0.5/1 to 5/1, and where the ratio of (b) to (a) is in the range 0.6/1 to 1.5/1.

2. The process of claim 1 in which the compound is a methyl pentenoate and the product is methyl-5-formylvalerate.

3. The process of claim 1 in which the solvent is selected from the group consisting of acetonitrile, adiponitrile, methylglutaronitrile, dimethyladipate, valerolactone, methylisobutylketone, methylene chloride, mixtures of one of the above nitriles and toluene, and mixtures of the above nitriles and water.

4. The process of claim 1 in which the temperature is in the range of 80° to 120° C. and the carbon monoxide partial pressure is in the range of 250 to 3000 pounds per square inch.

5. The process of claim 1 in which the compound is selected from the group consisting of methyl-3-pentenoate, and 3-pentenenitrile, and the bidentate diaryl phosphine ligand having the formula Ar2P—Q—PAr2 is 1,1'-bis(diphenylphosphino)ferrocene.

6. The process of claim 1 in which the acid component of the catalyst is trifluoromethanesulfonic acid.

7. A process for the preparation of acetals of 5-formylvaleric acid, 5-formylvaleric acid ester or 5-formylvaleronitrile which comprises contacting a compound selected from the group consisting of 2-, or 3-pentenoic acid, 2-, or 3-pentenoic acid ester and 2-, or 3-pentenenitrile, with hydrogen and carbon monoxide in a primary or secondary alcohol having up to 6 carbon atoms containing a dissolved catalyst comprising (a) a platinum compound free of anionic halide, (b) a bidentate diaryl phosphine ligand having the formula Ar2P—Q—PAr2 where Q is a bivalent bridging group containing 3–5 carbon atoms in which 2 or 3 carbon atoms of the bridge may be part of a cycloalkyl ring containing 3 to 6 carbon atoms or is a ferrocenyl group and each Ar group contains 6 to 15 carbon atoms and (c) an acid promoter selected from (1) sulfonic acids having a pKa in water of less than −2, (2) tetrafluoroboric acid, (3) a fluorine substituted aryl boronic acid of the formula: [HZ]+[B(Ph)4]− where Z is an oxygen containing Lewis base and Ph is a fluorine or trifluoromethyl substituted phenyl group, and (4) hexafluorophosphoric acid and where the ratio (c) to (a) is in the range 0.5/1 to 5/1, and where the ratio of (b) to (a) is in the range 0.6/1 to 1.5/1.

* * * * *